(12) United States Patent
Doe et al.

(10) Patent No.: US 7,168,299 B2
(45) Date of Patent: Jan. 30, 2007

(54) HEAT SPREADER FOR ROTARY RHEOMETER

(75) Inventors: Nigel Doe, Horsham (GB); Peter Foster, Lingfield (GB)

(73) Assignee: Waters Investments Limited, New Castle, DE (US)

( * ) Notice: Subject to any disclaimer, the term of this patent is extended or adjusted under 35 U.S.C. 154(b) by 93 days.

(21) Appl. No.: 11/075,338

(22) Filed: Mar. 9, 2005

(65) Prior Publication Data
US 2005/0199044 A1  Sep. 15, 2005

Related U.S. Application Data

(60) Provisional application No. 60/551,331, filed on Mar. 10, 2004.

(51) Int. Cl.
*G01N 11/00* (2006.01)
(52) U.S. Cl. .................................... 73/54.43
(58) Field of Classification Search ............... 73/54.37, 73/54.39, 54.43
See application file for complete search history.

(56) References Cited

U.S. PATENT DOCUMENTS

| | | | |
|---|---|---|---|
| 4,630,468 A | 12/1986 | Sweet | |
| 4,829,830 A * | 5/1989 | Tosaki | 73/847 |
| 4,878,377 A | 11/1989 | Abel | |
| 4,878,379 A * | 11/1989 | Deer | 73/54.39 |
| 5,777,212 A | 7/1998 | Sekiguchi et al. | |
| 6,571,610 B1 * | 6/2003 | Raffer | 73/54.35 |
| 6,572,610 B2 | 6/2003 | Kovalcheck et al. | |

OTHER PUBLICATIONS

Don Palazek "Magnetic Bearing Torsional Crepp Apparatus" Journal of Polymer Science, A2 6:621-638.

* cited by examiner

*Primary Examiner*—Daniel S. Larkin
(74) *Attorney, Agent, or Firm*—Paul, Hastings, Janofsky, & Walker, LLP; Aslan Baghdadi, Esq.

(57) ABSTRACT

A rotary rheometer having a an upper heating/cooling assembly and a lower heating/cooling assembly located opposite one another opposite a sample gap. The lower heating/cooling assembly may comprise a Peltier heater and the upper heating/cooling assembly preferably comprises a heating element that mates with a heat spreader for heating and cooling the area above the sample and providing more uniform heating and cooling across the sample gap while also minimizing any chimney effect within the rheometer and/or providing heating/cooling capability that is insensitive to changes in the gap between an upper geometry and the lower heating/cooling assembly. The upper heating/cooling assembly may further comprise a cooling channel for cooling the upper heating/cooling assembly.

21 Claims, 5 Drawing Sheets

HEAT SPREADER FOR ROTARY RHEOMETER

This application claims the benefit of U.S. Provisional Application No. 60/551,331, filed Mar. 10, 2004, which is herein incorporated by reference in its entirety.

BACKGROUND

1. Field of the Invention

The present invention relates generally to rheometers, which are used to characterize materials by measuring the materials' viscosity, elasticity, shear thinning, yield stress, compliance and/or other material properties.

2. Background of the Invention

Rotary rheometers, viscometers or viscosimeters are used to measure fluid or other properties of materials, such as their viscosity, by rotating, deflecting or oscillating a measuring object in a material, and measuring, for example, the torque required to rotate or deflect or oscillate the object within the material. As used herein, the term "rheometer" shall mean rheometers, viscometers, viscosimeters and similar instruments that are used to measure the properties of fluid or similar (see list below) materials.

The term "measuring object" shall mean an object having any one of several geometries, including, for example, cones, discs, vanes, parallel plates, concentric cylinders and double concentric cylinders. The materials may be liquids, oils, dispersions, suspensions, emulsions, adhesives, biological fluids such as blood, polymers, gels, pastes, slurries, melts, resins, powders or mixtures thereof. Such materials shall all be referred to generically as "fluids" herein. More specific examples of materials include asphalt, chocolate, drilling mud, lubricants, oils, greases, photoresists, liquid cements, elastomers, thermoplastics, thermosets and coatings.

As is known to one of ordinary skill in the art, many different geometries may be used for the measuring object in addition to the cylinders, cones, vanes and plates listed above. The measuring objects may be made of, for example, stainless steel, anodized aluminum or titanium. U.S. Pat. No. 5,777,212 to Sekiguchi et al., U.S. Pat. No. 4,878,377 to Abel and U.S. Pat. No. 4,630,468 to Sweet describe various configurations, constructions and applications of rheometers.

The fluid properties of materials are generally dependent on their temperature. For that reason, it is generally important that the temperature of the material being tested is known and is homogeneous. If the temperature of the material being tested were not homogeneous, the accuracy and validity of the measurement would be seriously compromised. Thus, the temperature of the fluid is generally accurately controlled, and is preferably made as homogeneous as possible, for example by using a fluid bath or a Peltier plate. Compared to a fluid bath, a Peltier plate temperature control system provides a more rapid heating and cooling of the sample, and is more economical, because it does not require an expensive controlled-temperature fluid circulator.

FIG. 1A is a schematic perspective view of a prior art rotary rheometer 100, showing lead screw 101, draw rod 102, optical encoder 103, air bearing 104, drive shaft 105, drag cup motor 106, measuring object 107 (shown in FIG. 1A as a parallel plate), heating/cooling assembly (e.g., a Peltier plate) 108, temperature sensor 110 (e.g., a Pt temperature sensor), surface 111, normal force transducer 112, and auto gap set motor and encoder 113. FIG. 1B is a schematic drawing of a concentric cylinder configuration in position on the rheometer of FIG. 1A, showing the control jacket 120 of the concentric cylinder configuration on top of normal force transducer 112 of rheometer 100. FIG. 1B shows a cylindrical measuring object 121 (used in this configuration instead of the parallel plate measuring object 107 shown in FIG. 1A). In operation, control jacket 120 contains a sample cup.

As mentioned above, uniform heating of a sample is an important factor in obtaining accurate measurements. As with many prior art devices, the rheometer of FIG. 1A relies solely on a Peltier heater 108 as the heat source to heat the sample from the bottom. Controlling the temperature from just one side of the sample in this manner can introduce error. As testing moves further away from ambient temperatures, error may increase due to the likelihood of increased temperature gradients. Increasing geometry gap as well as increasing temperature sensitivity of the sample may also increase error. For many applications, especially those occurring near ambient temperature, the error associated with single-side heating is insignificant.

As testing is done away from ambient temperatures, it becomes more desirable to have more uniform heating thus making heating from more than just the lower plate desirable. One example of a prior art device that utilizes multi-station heating is disclosed in U.S. Pat. No. 6,571,610. That disclosure teaches the use of an upper Peltier plate used in combination with a lower Peltier heating plate to achieve more uniform heating and cooling of a sample. Peltier plates may not, however, be the most desirable manner of heating the upper geometry of a rheometer. Such Peltier heating as disclosed in U.S. Pat. No. 6,571,610 can create a chimney effect whereby colder ambient air is drawn toward the heating element and exhausted out the top of the device. Such a flow of air can lead to undesirable cooling or simply affect heating of the sample such that the measurements taken become less accurate.

Further, the heat spreader of U.S. Pat. No. 6,571,610 moves relative to the upper Peltier heater as necessary to accommodate an increased or decreased sample gap. Because the heat spreader does not remain at a constant distance from the Peltier heater, the heating profile of the heat spreader, and thus the sample being tested, is constantly changing. This constantly changing difference in heating capability requires recalibration of the rheometer practically every time a new sample is tested. It would be desirable to have a rheometer with upper geometry heating capabilities that overcomes the drawbacks, such as chimney effect and sensitivity of the heat transfer function to geometry gap, of prior art rheometers.

SUMMARY OF THE INVENTION

The present invention is a rotary rheometer having an upper assembly including active heating element(s) to heat the sample from more than just the bottom plate. One consideration in rheometer design is that there must be no contact between the upper heated plate assembly and the upper geometry heat spreader. The design, must therefore include an efficient method of transferring heat and cold. In the present invention, this is accomplished by placing heating elements in communication with a heat spreader to transfer the heat to the upper geometry. The upper heating assembly, according to an exemplary embodiment includes a pair of interlocked or mated elements that can be calibrated and employed to actively heat the sample gap from the above in addition to the lower heating plate. Several advantages arise from this configuration, including minimization of inertia, maximization of surface area for temperature transfer, and reduction of chimney effect. A further advantage of embodiments of the present invention is that their design is insensitive to changes in geometry gap or diameter, so calibration and re-calibration is kept to a minimum. The temperature of the upper plate may further be modeled and the lower plate matched to it. Such matching causes the two plates to remain closely coupled during temperature ramps, thus meaning that the temperature displayed by the rheometer is that of both plates, not just the lower one.

DETAILED DESCRIPTION OF THE INVENTION

Figure 1A:
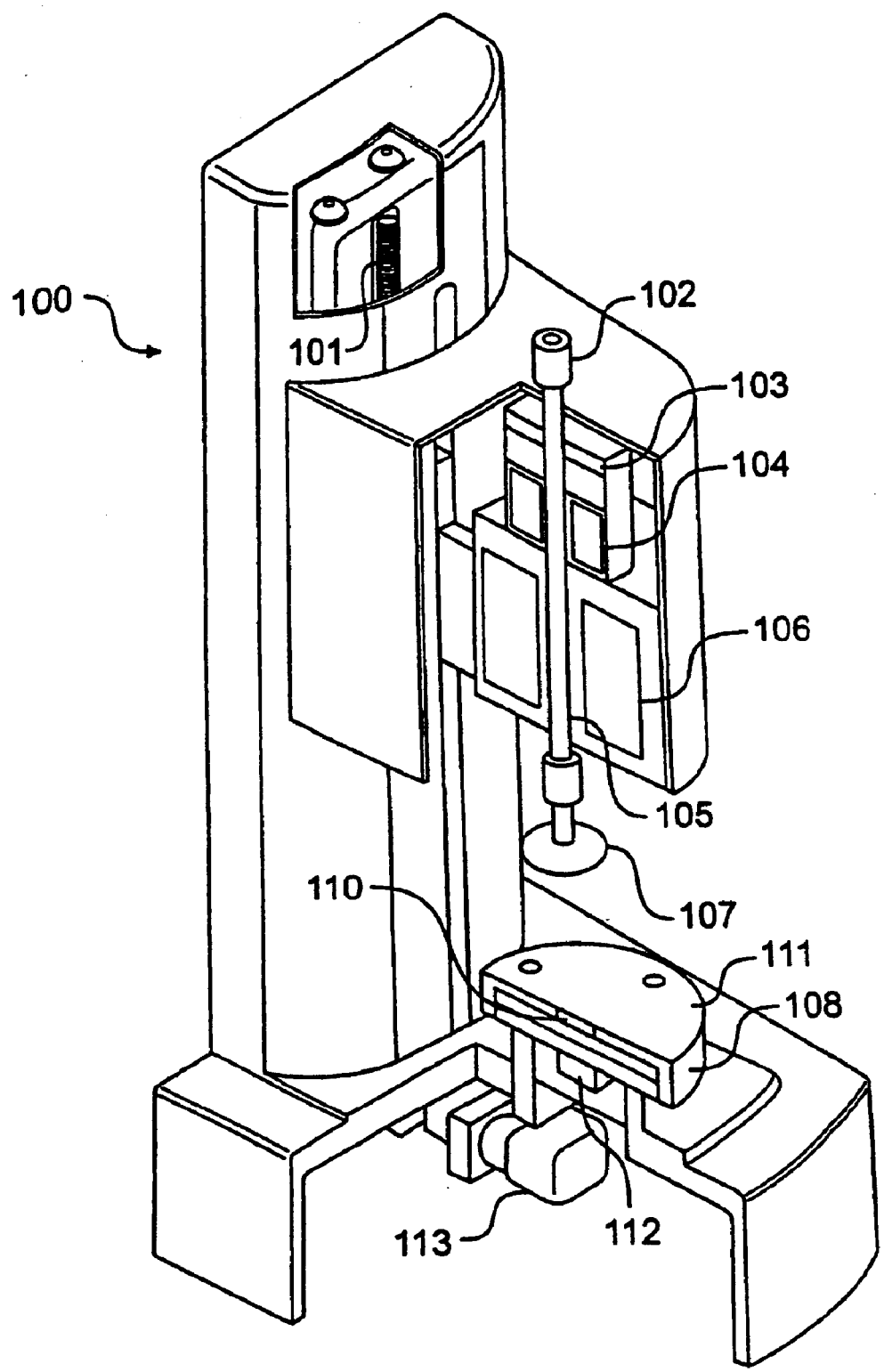
FIG. 1A is a schematic diagram of a perspective view of a prior art rotary rheometer.
Figure 1B:
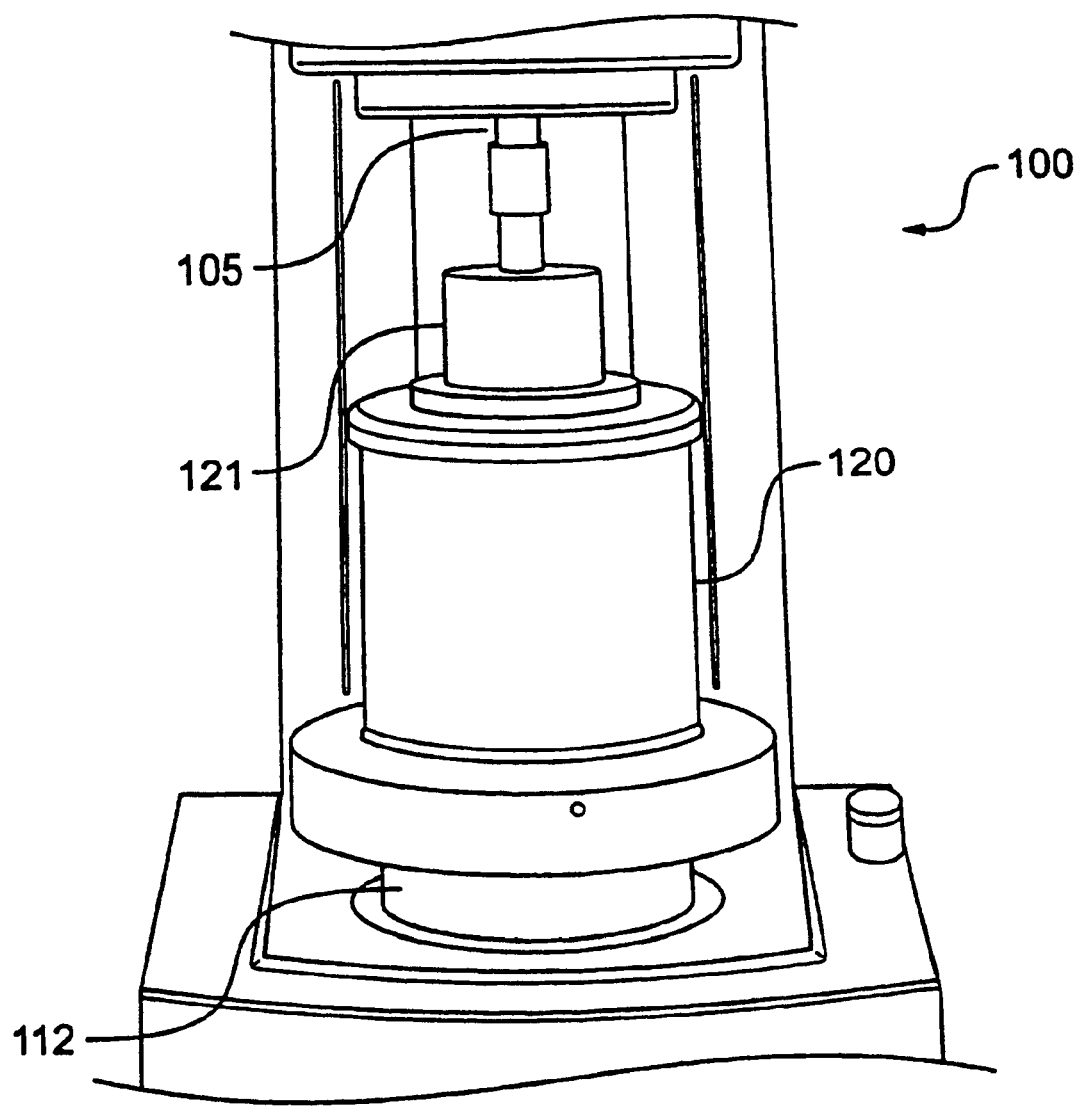
FIG. 1B is a schematic diagram of a concentric cylinder configuration in position on the rheometer of FIG. 1A.
Figure 2:
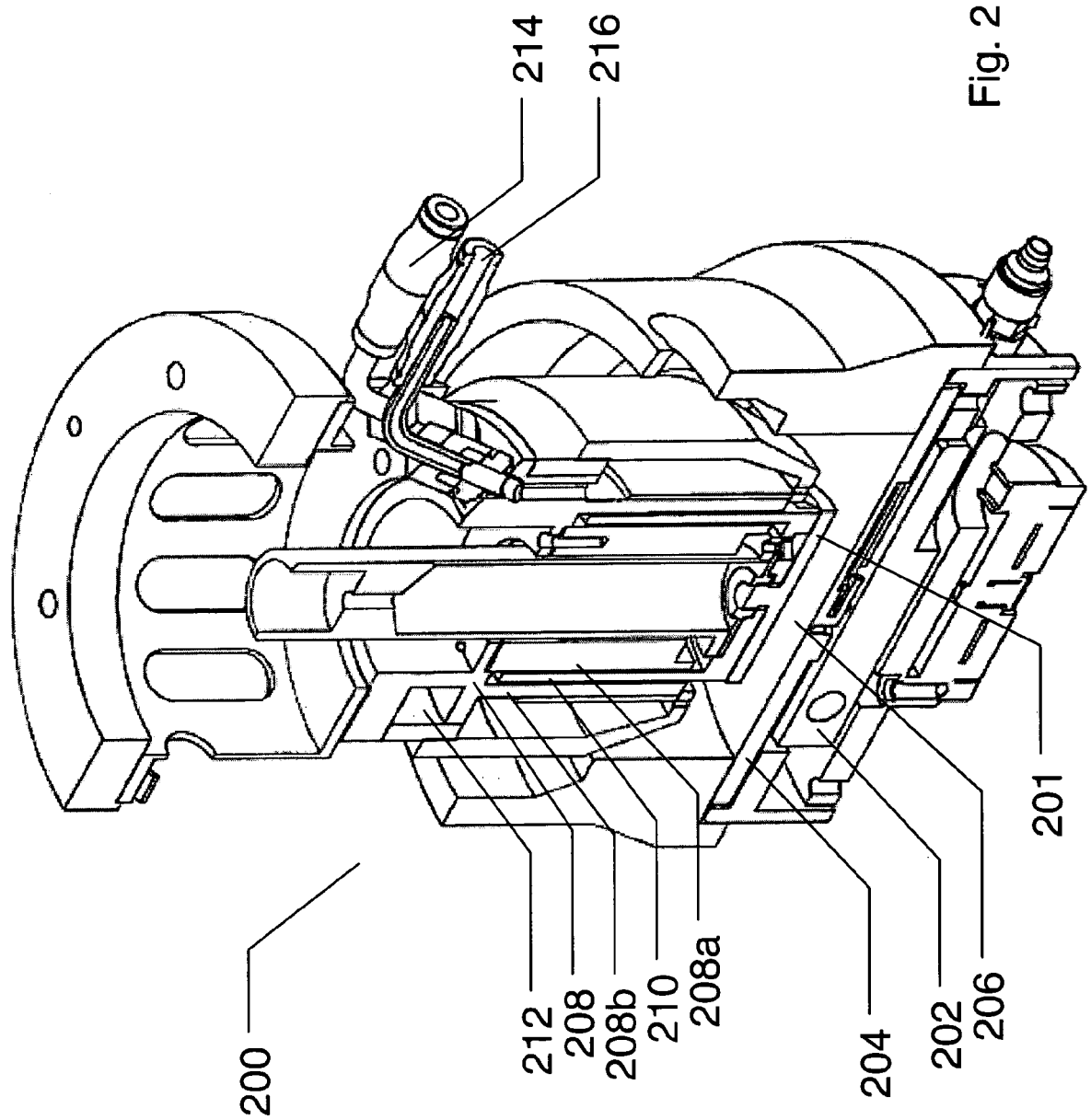
FIG. 2 is a schematic diagram of a perspective view of a rotary rheometer according to an exemplary embodiment of the present invention.

FIG. 2 is a perspective cut-away schematic diagram that shows an exemplary embodiment of the upper geometry heater of the present invention. As shown, rheometer 200 is similar in most functional rehometry aspects as prior art devices. It includes upper geometry 201, a Peltier plate heater 202, a lower heat spreader 204 for distributing the heat generated by heater 202 to sample gap 206, which is located between the upper geometry 201 of rheometer 200 and lower heat spreader 204. Above sample gap 206, however, is an upper heat plate assembly 208 comprising an inner portion 208a and an outer portion 208b. Inner portion 208a and outer portion 208b combine to form an inverted "U" shaped heating element. One of skill in the art will understand the inner portion 208a and outer portion 208b may comprise a single unitary element or may comprise separate elements that may or may not be connected to one another. Upper heat plate assembly 208 fits over upper geometry heat spreader 210, which takes the shape of an upright "U". As with elements 208a and 208b, element 210 may also comprise a single unitary element or may comprise multiple elements that may or may not be physically connected to one another. Mating element 208 with element 210 in this fashion minimizes the chimney effect often encountered with prior art devices having upper geometry heating. Also, as described above, this configuration takes into account the design factor that elements 208a and 208b must not be in direct contact with upper geometry 201.

In addition to minimizing the chimney effect and providing the desirable non-contact design, upper heat plate assembly 208 and upper geometry heat spreader 210 maintain a constant relationship with upper geometry 201. As the sample gap is increased, by moving the upper assembly up or down, heat plate assembly 208, upper geometry heat spreader 210, and upper geometry 201 all move together. In this manner, the heat transfer function from upper heat plate assembly 208 to upper heat spreader 210 and upper geometry 201 is always the same, thus eliminating the need for calibration of the device as sample gap is changed.

Upper heat plate assembly 208 can advantageously be cooled by various methods depending on the temperature range required. Such cooling can be done by, for example, introduction of air, water, chilled fluid or vortex cooling. To aid in the cooling, assembly 208 further includes a cooling channel 212 for circulating a cooling fluid as described above. Cooling channel 212 is connected to coolant inlet 214 for introduction of an appropriate cooling fluid. Also, not pictured, rheometer 200 includes a cooling outlet for evacuation of the cooling fluid. An additional inlet 216 is provided for evacuation of inert gas.

Due to the heating elements used in upper assembly 208, lower Peltier plate 202 can ramp up and down in temperature faster than that of upper assembly 208. In order to accommodate for this potentially uneven heating, the heating of the upper geometry may be modeled and then lower Peltier plate 202 can be matched so as to heat and cool in the same manner as upper assembly 208. Such matching between the two heat sources results in a minimization of temperature gradients during temperature ramps.

Figure 3A:
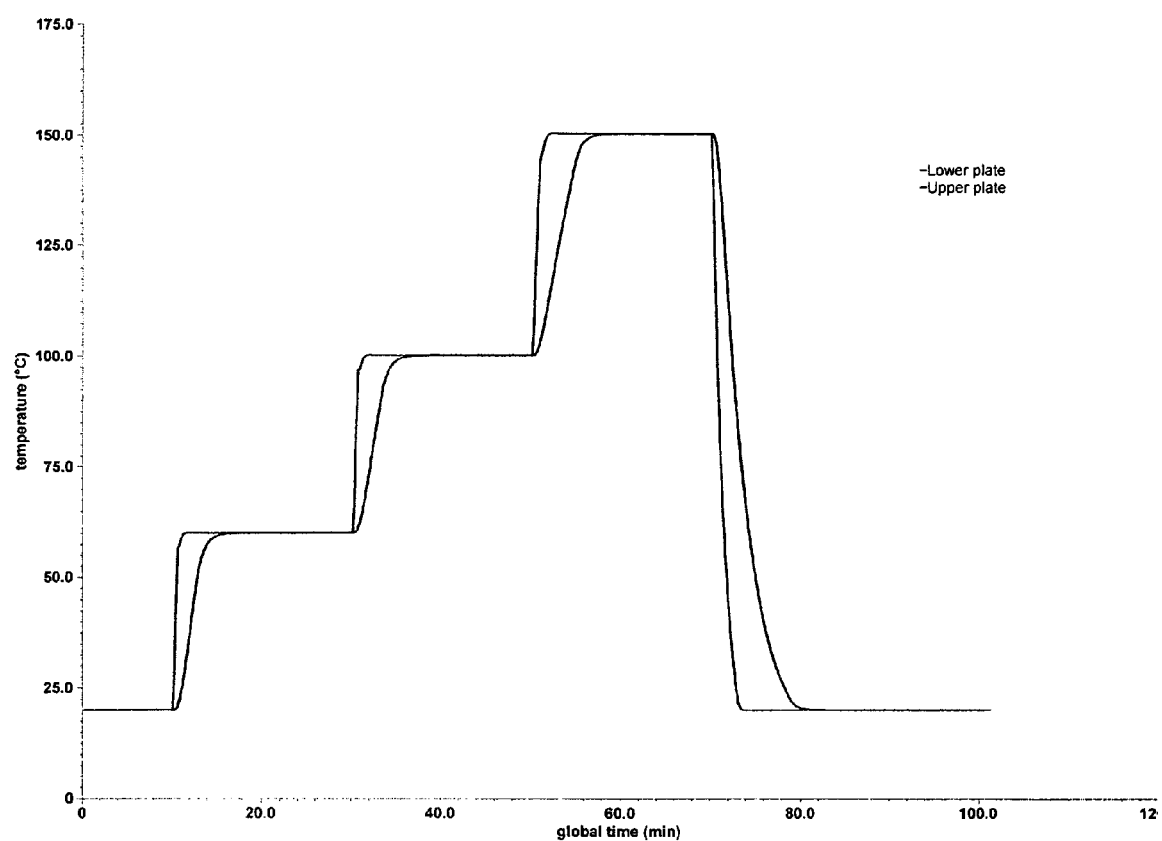
FIGS. 3A and 3B are graphical representations of temperature ramps showing comparisons between the ramping of unmatched and matched upper and lower heat plates.
Figure 3B:
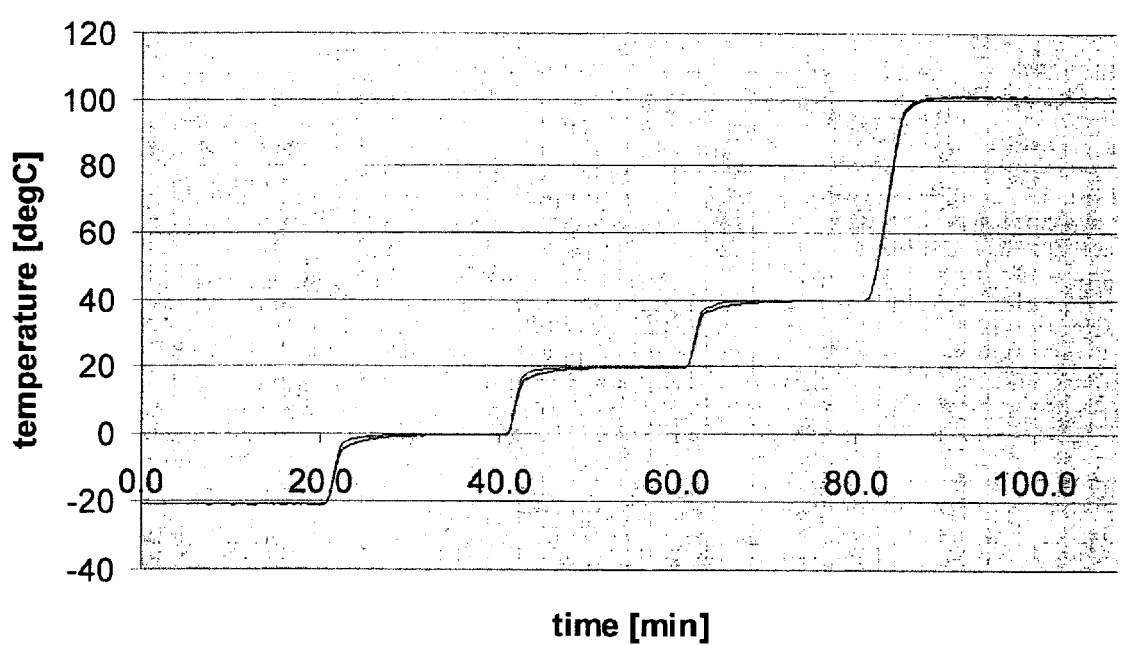

This temperature matching also means that whatever temperature is displayed is that for both the upper assembly 208 and lower Peltier heating plate 202, whereas in prior art devices, only the temperature of the lower Peltier plate is usually measured. FIGS. 3A and 3B show graphical representations of upper and lower heating before and after calibration of lower Peltier plate 202 heating to the model of the upper plate heating assembly 208. As shown, the two heating devices are nearly identical in FIG. 3B, thus greatly minimizing any temperature gradient between the two heating elements. Also, because any chimney effect is greatly reduced, if not eliminated, any temperature gradient of the sample is further reduced.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

What is claimed is:

1. A rheometer comprising:
   an upper heating/cooling assembly located above a sample gap; and
   a lower heating/cooling assembly located below the sample gap,
   wherein the upper heating/cooling assembly maintains a constant relationship with an upper geometry as the sample gap is changed, and wherein the upper heating/cooling assembly comprises at least a first substantially cylindrical heating element positioned within a substantially cylindrical heat spreader.

2. The rheometer of claim 1, further comprising a gap formed between the first substantially cylindrical heating element and the substantially cylindrical heat spreader.

3. The rheometer of claim 1, wherein the upper heating/cooling assembly further comprises a second substantially cylindrical heating element, wherein the substantially cylindrical heat spreader is positioned within the second substantially cylindrical heating element.

4. The rheometer of claim 3, further comprising a gap formed between the heat spreader and the second heating element.

5. The rheometer of claim 3, wherein the first and second heating elements comprise a single heating element formed in an inverted U-shape around the heat spreader.

6. The rheometer of claim 5, further comprising a gap formed between the single heating element formed in an inverted U-shape and the heat spreader.

7. The rheometer of claim 1, further comprising a gap formed between the first substantially cylindrical heating element and the substantially cylindrical heat spreader.

8. The rheometer of claim 1, wherein the upper heating/cooling assembly does not comprise a Peltier heater.

9. The rheometer of claim 8, wherein the lower heating/cooling assembly is substantially matched to a model of the upper heating/cooling assembly.

10. The rheometer of claim 9, wherein the lower heating/cooling assembly comprises a Peltier heater.

11. The rheometer of claim 1, further comprising a cooling channel for cooling the upper heating/cooling assembly.

12. The rheometer of claim 1, wherein the upper heating/cooling assembly is configured to minimize a chimney effect within the rheometer.

13. A rheometer, comprising:
an upper heating/cooling assembly located above a sample gap; and
a lower heating/cooling assembly located below the sample gap,
wherein the upper heating/cooling assembly comprises an upright substantially U-shaped heat spreader mated with an inverted substantially U-shaped heating element.

14. The rheometer of claim 13, wherein the upper heating/cooling assembly does not comprise a Peltier heater.

15. The rheometer of claim 13, wherein the lower heating/cooling assembly is substantially matched to a model of the upper heating/cooling assembly.

16. The rheometer of claim 13, further comprising a cooling channel for cooling the upper heating/cooling assembly.

17. The rheometer of claim 13, wherein the upper heating/cooling assembly maintains a constant relationship with an upper geometry as the sample gap is changed.

18. An upper heating/cooling assembly for use in a rheometer opposite a lower heating/cooling assembly, comprising an upright substantially U-shaped heat spreader mated with an inverted substantially U-shaped heating element.

19. The upper heating/cooling assembly of claim 18, wherein the heating element does not comprise a Peltier heater.

20. The upper heating/cooling assembly of claim 18, further comprising a cooling channel for cooling the upper heating/cooling assembly.

21. The upper heating/cooling assembly of claim 18, wherein the upper heating/cooling assembly is configured to maintain a constant relationship with an upper geometry as a sample gap is changed.

* * * * *